United States Patent [19]

Kercso

[11] 4,105,030
[45] Aug. 8, 1978

[54] IMPLANT APPARATUS

[75] Inventor: Josef E. Kercso, Palo Alto, Calif.

[73] Assignee: Syntex (U.S.A.) Inc., Palo Alto, Calif.

[21] Appl. No.: 756,450

[22] Filed: Jan. 3, 1977

[51] Int. Cl.² ............................................. A61M 5/18
[52] U.S. Cl. ................................................... 128/217
[58] Field of Search ................. 128/217, 221, 213, 260

[56] References Cited

U.S. PATENT DOCUMENTS

| 2,512,569 | 6/1950 | Saffir | 128/221 |
| 2,907,327 | 10/1959 | White | 128/217 |
| 3,538,916 | 11/1970 | Wiles et al. | 128/217 |
| 3,774,607 | 11/1973 | Schmitz | 128/217 |

*Primary Examiner*—John D. Yasko
*Attorney, Agent, or Firm*—Tom M. Moran; William B. Walker

[57] ABSTRACT

Apparatus for subcutaneously implanting drug-containing pellets in animals. The apparatus comprises a handle; attached to the handle, a track along which a carriage moves; a carriage which moves along the track, the carriage having (i) a front part adapted to receive and retain a detachable needle having a passageway extending the length of the needle and (ii) a passageway extending the length of the carriage and corresponding to the needle passageway when retained in the carriage; a means to propel the carriage from the front to the rear of the track; means at the front and rear of the track to stop the carriage; a straight, retractable rod detachably attached to the rear stopping means so that the rod extends straight through the carriage passageway; a finger actuatable trigger attached to the handle to actuate the retraction of the carriage. A unique, flanged needle having a sharp metal end, an enlarged, flanged end, a passageway extending the length of the needle, and at least one pellet in the needle passageway is also described.

12 Claims, 20 Drawing Figures

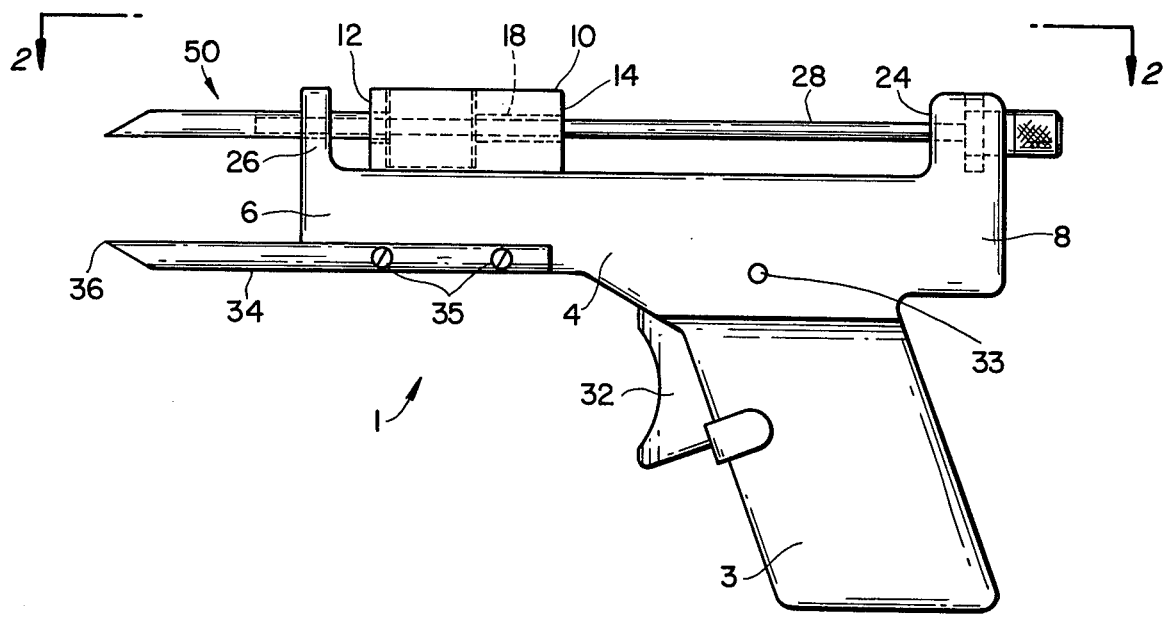
FIG_1
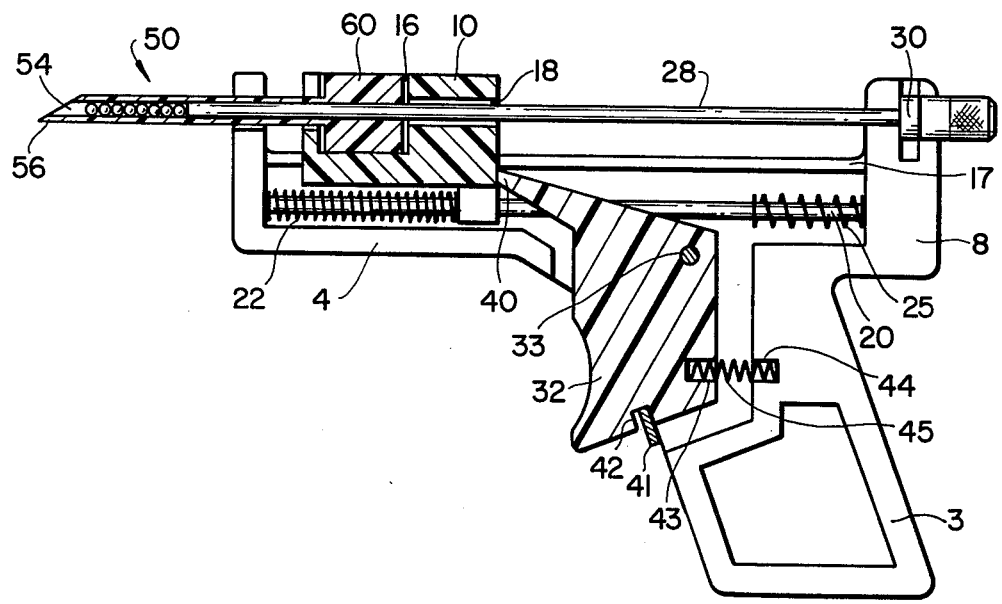
FIG_5

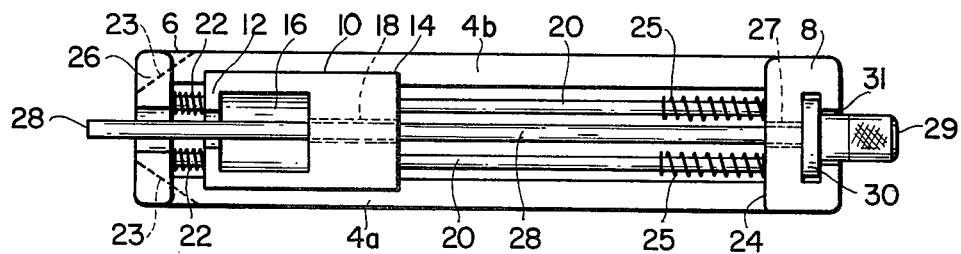
FIG_2a
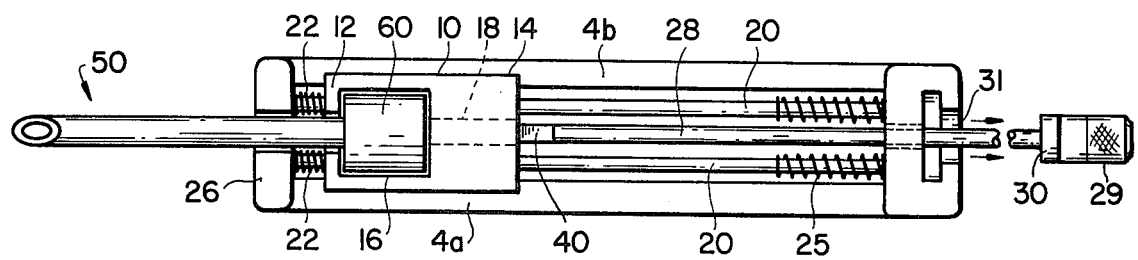
FIG_2b
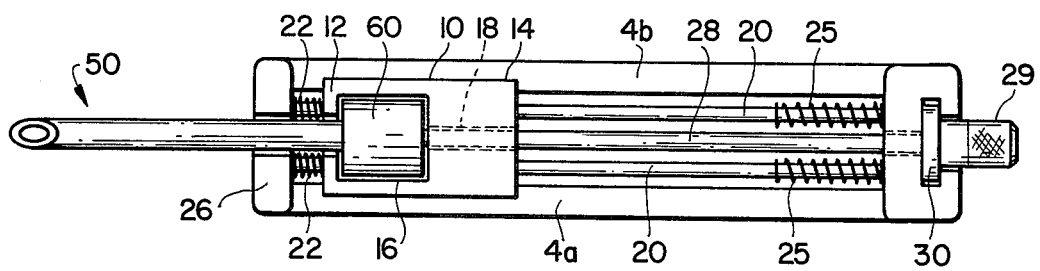
FIG_2c
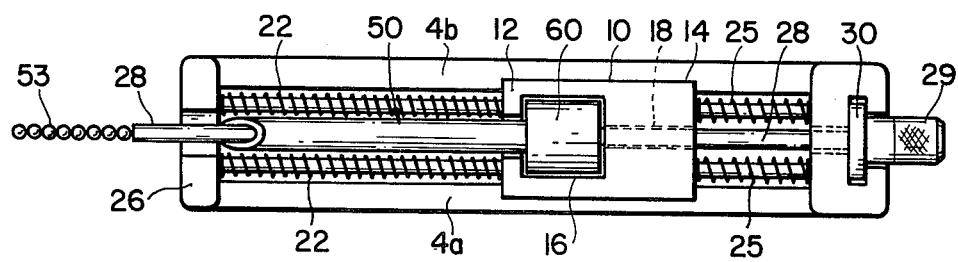
FIG_2d

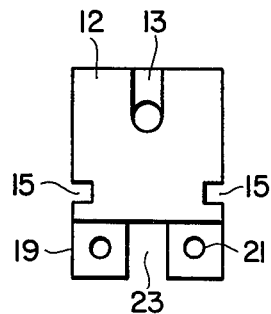
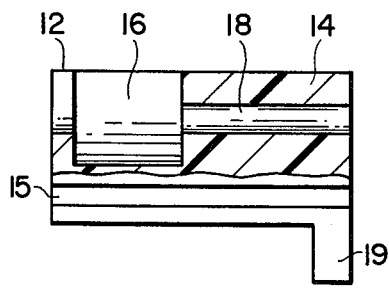
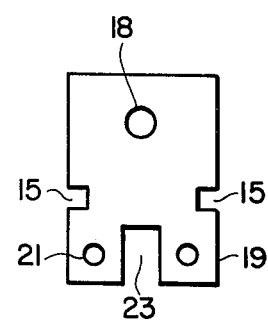
FIG_3b     FIG_3a     FIG_3c
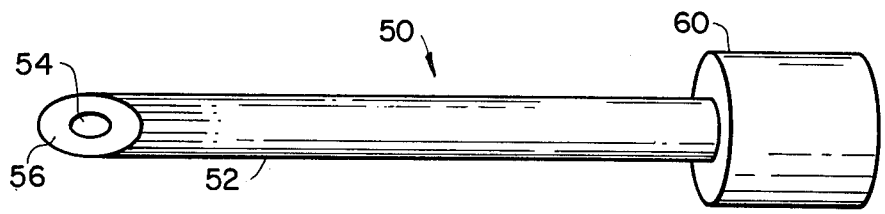
FIG_4a
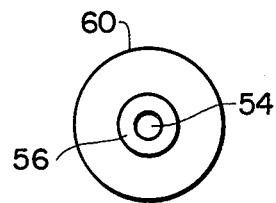     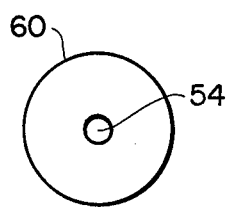
FIG_4b     FIG_4c
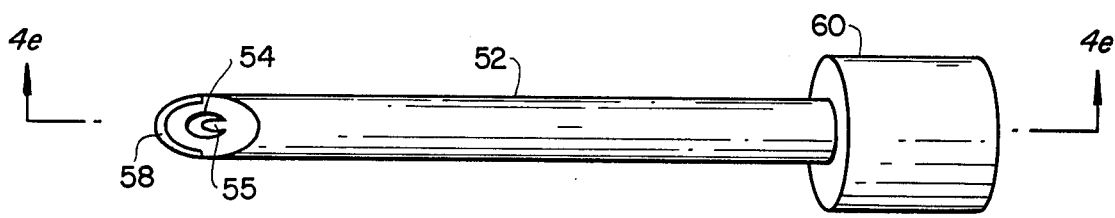
FIG_4d
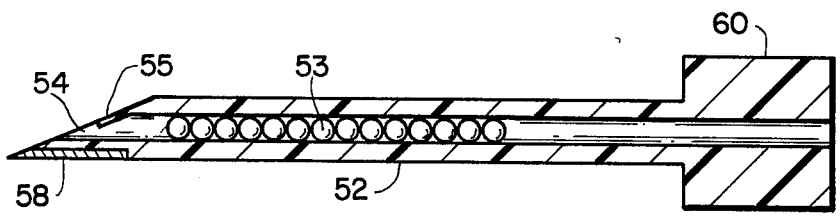
FIG_4e

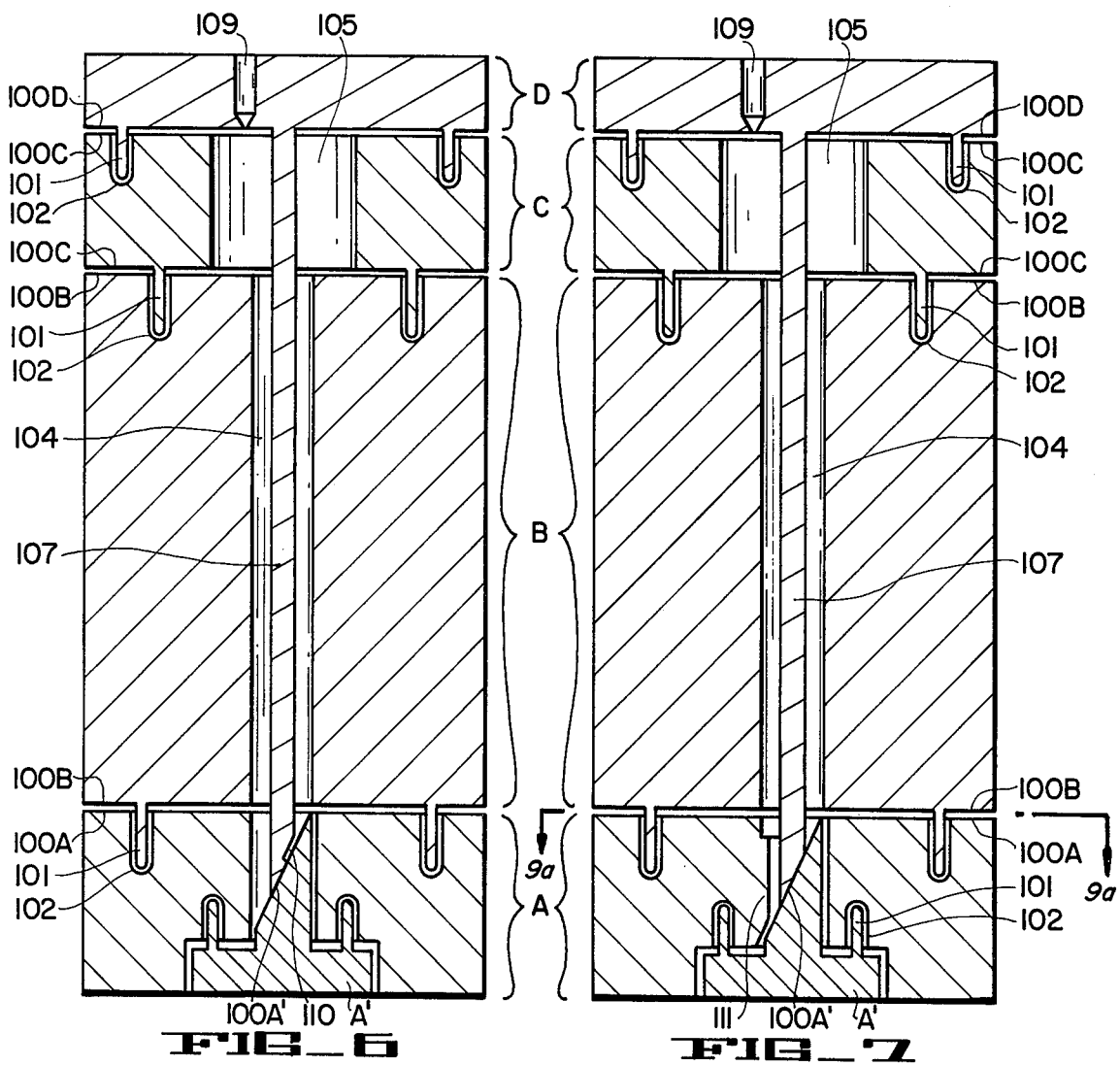
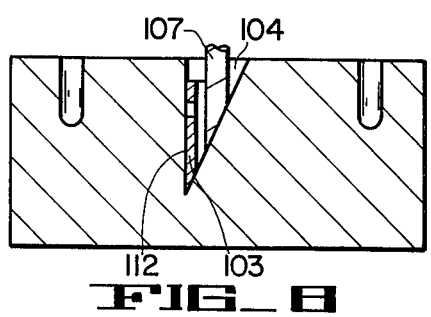
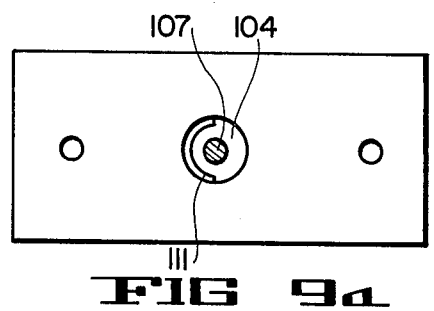
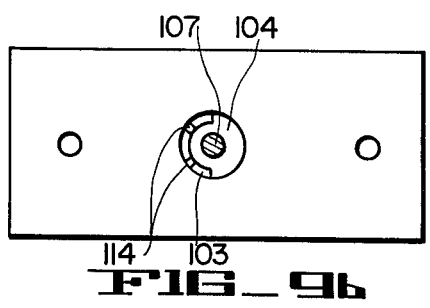
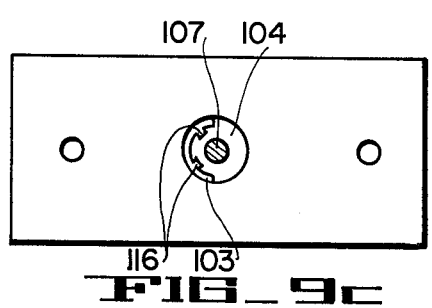

IMPLANT APPARATUS

BACKGROUND OF THE INVENTION

1. Field of the Invention

This invention relates to an apparatus and process useful for subcutaneously implanting biologically acceptable pellets in animals. More specifically, it relates to an apparatus which allows a needle containing the pellets to be subcutaneously inserted in the animal, then retracted from around the pellets, thus implanting the pellets.

2. Prior Art

It is generally known in the art that it is desirable in some cases to subcutaneously implant medicament containing pellets in some domestic animals such as cattle, sheep, horses, pigs, etc., to obtain a desired result such as weight gain, contraception, estrus suppression, or disease treatment. In the past pellets were implanted using devices wherein the pellets were pushed out of a needle using a plunger of some sort. With these devices, one would either (a) insert the needle to the desired depth to establish a subcutaneous channel then force the pellets out of the needle while manually withdrawing the needle and device to deposit the pellets along the channel or (b) insert the tip of the needle subcutaneously then force the pellets under the skin, the pellets forming a channel themselves as they are forced out. In either case much pressure is placed on the pellets and they would disintegrate, crack or otherwise become damaged upon deposition to alter the delivery characteristics, unless great care was taken. In the case where a plurality of pellets were to be implanted from one needle, sometimes all the pellets could not be deposited at one place. Patents which represent these devices include U.S. Pat. No. 2,907,327 to White; Australian Pat. No. 253,175 to Boots Pure Drug Co.; U.S. Pat. Nos. 1,347,622 to Deininger; 2,761,446; 2,883,984 to Candido et al.; 3,058,465 to Bell; 3,402,712 to Eisenhand; 3,520,299 to Lott et al.; 3,538,916 to Wiles; 3,669,104 to Wyatt et al.; 3,774,607 to Schmitz; and 3,921,632 to Bardani.

The difficulties inherent in the prior art can be substantially eliminated by the apparatus and process of the present invention. In the apparatus of this invention, the pellet-containing needle is attached to a carriage which is retracted after the needle is subcutaneously inserted in the animal, thus leaving the pellet or pellets implanted in the animal in the channel preformed by the insertion of the needle.

SUMMARY OF THE INVENTION

The apparatus of this invention comprises a handle to grasp the apparatus; attached to the handle, a track along which a carriage moves; a carriage which moves along the track, the carriage having (i) the front part of said carriage adapted to receive and retain a detachable needle having a passageway extending the length of the needle, (ii) a passageway extending the length of said carriage parallel to the length of the track and corresponding to the needle passageway when the needle is received and retained in said carriage, and (iii) means to guide and stabilize the carriage in the track; a means to propel the carriage from the front to the rear of the track; means at the rear of the track to stop the carriage when propelled rearwardly; means attached to the front of the track to retain the carriage; a straight, retractable rod attached to the rear stopping means so that the rod extends straight through the carriage passageway; means to retain or retract the rod; a finger actuatable trigger attached to the handle to actuate the retraction of the carriage. Preferably, the carriage of the apparatus has a recess in the front part of the carriage and is combined with a unique flanged needle having a sharp end, an enlarged, flanged end, a passageway extending the length of the needle, and at least one pellet in the needle passageway so that the needle is received and retained in said carriage recess and when said carriage is propelled rearwardly, said rod extends beyond the sharp end of said needle.

The apparatus is particularly valuable for simultaneously depositing a plurality of spherical pellets from a plastic needle. The needle is preferably plastic and exhibits a high percentage of glass or metal particles to allow the point to be more easily sharpened or has a metal tip to aid in penetrating said animal's skin.

BRIEF DESCRIPTION OF THE DRAWINGS

FIG. 1 is a planar side view of the apparatus of this invention.

FIG. 2a is a top planar view of the apparatus of FIG. 1 without the needle.

FIG. 2b is a top planar view of the apparatus of FIG. 1 with the ejection rod retracted and a needle inserted.

FIG. 2c is the top planar view of the apparatus of FIG. 1 wherein the apparatus is loaded and ready to use.

FIG. 2d is a top planar view of the apparatus of FIG. 1 after the carriage has been retracted.

FIG. 3a is a side planar view of the carriage of the apparatus.

FIG. 3b is a front view of the carriage for the apparatus of this invention.

FIG. 3c is a rear planar view of the carriage for the apparatus of this invention.

FIG. 4a is a side perspective view of the needle which is useful in the apparatus of this invention.

FIG. 4b is a front view of the needle of FIG. 4a.

FIG. 4c is a rear planar view of the needle of FIG. 4a.

FIG. 4d is a side perspective view of a needle of this invention wherein the needle has a metal tip at the sharp end of the needle.

FIG. 5 is a side view of a vertical cross-section of the apparatus of FIG. 1.

FIG. 6 is a planar view of a vertical cross-section of a mold employed for injection molding a needle of FIG. 4a.

FIG. 7 is a planar view of a vertical cross-section of a mold employed for injection molding a needle of FIG. 4d.

FIG. 8 is a planar view of a vertical cross-section of the lower quarter of a mold employed for injection molding a needle of FIG. 4d.

FIGS. 9a–9c are planar views of a horizontal cross-section of the lower quarter of a mold employed for injection molding a needle of FIG. 4d.

DESCRIPTION OF PREFERRED EMBODIMENTS

Referring first to FIG. 1, we see a planar side view of the apparatus of this invention which is suitable for subcutaneously implanting at least one, and preferably a plurality of pharmaceutically acceptable pellets in an animal. The pellets, which are implantable by this invention, may be a single cylinder, a series of small cylinders, or preferably a series of small spheres. The pellets which are subcutaneously implanted in the animal produce a weight gain in the animal if the active ingredient in the pellet is an anabolic agent, control estrus, prevent conception, or deliver a drug to the animal over a period of time in a controlled manner. Thus, the pellets must be pharmaceutically acceptable in that they are not rejected by the animal and comprise ingredients which are non-toxic and create the desired result in the animal implanted. The pellets are shown in FIGS. 2 d, 4e and 5 as spheres.

The apparatus consists of a handle means 3 for grasping the apparatus with one hand. Attached to said handle means and preferably integral therewith is a track 4 having a front part 6 and rear part 8. Only the exterior of the track is shown in FIG. 1, but the track is generally suitable for a carriage 10 to move therealong on the inside of the track portion, the carriage 10 being retained by walls 4a and 4b in FIG. 2a. Thus, the track portion encompasses both the outside portion as well as the inside portion of the track along which the carriage 10 moves.

The carriage 10 is retained within the track and is movable therealong and has a front end 12 and back end 14 which correspond to the front and rear parts of the track. The carriage 10 has a means in the front part of the carriage by which a detachable needle is secured. The needle may be threaded and screwed into corresponding threads in the carriage or may be grooved to allow extensions of the carriage which correspond to the grooves to retain the needle. In the preferred embodiment, however, the carriage has recess 16 in the front part of the carriage which is adapted to receive and retain a flanged detachable needle 50 as shown by the dotted lines in FIG. 1 and further set forth in FIGS. 2a-2d and FIG. 3a. A passageway 18 extends the length of the carriage going through the back end 14, communicating with the recess 16 and continuing through the front portion 12 of the carriage. The carriage is guided and stabilized in the track by a means suitable for said purpose not shown in FIG. 1 but further discussed in the discussion of FIGS. 2a-2d and FIGS. 3a-3c.

The carriage is propelled along the track by a means not shown in FIG. 1 which moves the carriage from the front part of the track to the rear part. The means of propulsion may be a helical coil spring which pushes the carriage rearwards, a coiled spiral spring with one end attached to the rear of the carriage 10 to pull the carriage rearwards, or a cylinder of compressed gas to push the carriage back. The preferred means is a helical coil spring which pushes the carriage rearwards. A means 24 is attached to, or is an integral part of, the rear part of the track 4 to stop the carriage 10 when propelled rearwardly and a similar means 26 is attached to, or is an integral part of, the front part of the carriage to retain said carriage within the track.

A straight, solid retractable rod 28 is attached to the stopping means 24 in the rear part of the track so that the rod extends straight through the carriage passageway 18 and front retaining means 26. When the carriage is in the cocked, ready position in the front part of the track, a trigger 32 is actuated by pressing with the finger holding the handle means 3 to release the carriage and allow the spring to propel the carriage rearwardly along the track and rod 28 while holding the handle stationary with one hand. The trigger pivots on axle 33. Generally, the dimensions of the apparatus, excluding the rod 34 and needle 50, will be about 5-10 inches (preferably 6-7 inches) in length by about 4-6 inches in height.

In some cases it may be advantageous to have a solid metal rod 34 attached to the outside of track 4 by any suitable means such as bolts or screws 35. The rod 34 has a sharp, beveled end 36 which is that part of the rod opposite the attached end. This sharp end is used to pierce the animal's skin and form a subcutaneous channel if the needle 50 employed is not sharp enough or strong enough to perform that function. Although rod 34 is shown attached to track 4 by screws 35, it is desirable to design rod 34 to be retractable.

Turning now to FIGS. 2a-2d, a top view of the apparatus as taken along line 2—2 can be seen. The apparatus is shown without rod 34 attached. In FIG. 2a the carriage 10 is in the cocked position ready to eject the pellets except, of course, there is no needle in recess 16. The carriage 10 is propelled along the track, and stabilized by rods 20 which extend through the lower portion of the carriage as further described in the discussion of FIGS. 3a-3c. The rods are attached to the front retaining portion 26 of the track and the back, stopping means 24 of the track so that the carriage can smoothly slide forward and backward along said rods. The carriage is propelled rearwardly by spring 22 which is shown in the compressed stage. The carriage is stopped by the stopping means 24 and is cushioned by spring means 25 which encircle rods 20. The cushioning means are preferably included so that the force of the carriage moving rearwardly does not damage the track and stopping means. As is apparent from the Figures, the rods provide a means for retaining springs 22 and 25.

It can be seen that rod 28 extends through stopping wall 24, through passageway 18 shown by the dotted lines through the recess 16, through the front part of the carriage 12 and out through the front part 26 of the track. To load the apparatus, the rod 28 is withdrawn by grasping and turning the knob 29 so that the rod retaining means 30 is allowed to slip through rear groove 31 which extends part way through stopping means 24. The rod 28 is then retracted as shown by the arrows in FIG. 2b to a position sufficient to allow insertion of needle 50 having enlarged flange 60 into recess 16. In FIG. 2b the rod is pulled out of the passageway 18 entirely but this is not necessary in order to load the device. The carriage is retained in the cocked position by the sear or tip 40 of trigger 32, not shown. The needle 50 is then placed securely into recess 16 and the rod is then extended through passageway 18, and recess 16 where it goes through passageway 54 extending the length of the needle to rest adjacent the pellets in passageway 54, which are to be implanted in the animal.

FIG. 2c shows the apparatus ready to be actuated. The trigger 32 is then pulled to release carriage 10, and the springs 22, which previously were compressed, expand to propel the carriage 16 rearwardly retracting the needle from the pellets 53 and leaving the pellet in place implanted beneath the animal's skin. By employing the apparatus and process of this invention, the pellets are not crushed and are more readily placed beneath the animal's skin than using the implant gun which forces the pellet out beneath the animal's skin because the needle forms a channel immediately, which channel is filled by the pellets when the needle is retracted. As the carriage moves rearwardly, it is prevented from hitting the stopping means 24 in the rear part of the track by cushioning means such as springs 25. In some cases, it is preferable to taper the front end 26 of track 4, as shown by line 23 in FIG. 2a, to make insertion of the needle 50 easier.

Although the carriage 10 and track 4 of the apparatus are shown in block form, it is understood that it may be desirable to utilize a more streamlined form such as an oval, "u" shaped or circular cross-section. In such cases, the carriage may be designed to utilize bearing surfaces which do not employ stabilizing means such as rods 20 or lip 17 and groove 15 (as in FIGS. 3a and 5), but merely are machined or molded to allow the carriage to smoothly glide past the inside track surface.

Turning now to FIGS. 3a-3c, a more detailed description of the carriage 10 may be seen. FIG. 3a is a side planar view of a vertical cross-section of the carriage wherein it can be seen that passageway 18 extends through the back 14 of the carriage, through the recess and through the front part 12 of the carriage 10. Running longitudinally along the side of the carriage is a groove 15 into which a lip (17 in FIG. 5) of the track fits to support the carriage and stabilize it as it is propelled rearwardly along the track. Extension 19 extends downwardly from the back part 14 of the carriage 10. Passageway 21 extends through extension 19 to allow the carriage to slide along rod 20. Groove 23 is cut in extension 19 to allow the tip 40 of trigger 32 to pass under the carriage. When the trigger is pulled, the carriage is released and propelled by the expansion of springs 22 pushing against extension 19. Alternatively, rods 20 may be eliminated if spring 22 is housed in the body of carriage 10.

Turning now to FIGS. 4a-4e, various aspects of a needle 50 which is usable in the apparatus of this invention are set forth. FIG. 4a shows a side perspective of the needle 50 of this invention which comprises an elongated tube or barrel 52 having an enlarged portion 60 and a sharp, beveled end 56. Extending the length of the tube is passageway 54. FIG. 4b is a front view of the needle of FIG. 4a while FIG. 4c is the rear view. The needle 50 may be made of any suitable material such as metal or plastic but preferably for economic reasons is made of a suitable plastic. Since it is preferred that the tube be disposable, it should be an inexpensive plastic such as nylon, polypropylene, polyethylene, and the like. Because these plastics do not have a high tensil strength and are difficult to mill to a fine point, preferably the sharp, beveled end of the tube comrises a plastic mixed with a substantial amount of particulate filler such as glass, powdered metal, or metallic oxides which tend to make the plastic more millable and more readily sharpened to form a sharp point which can be utilized to subcutaneously pierce the animal's skin. Alternatively, a sharp metal point 58 may be integrally attached to the point of the plastic shaft 52 so that the metal can be readily milled to a sharp point which then aids in the subcutaneous penetration of the needle.

FIG. 4e is a planar view of the vertical cross-section of the needle set forth in FIG. 4a and clearly shows a passageway 54 extending the length of the needle and containing, in a portion thereof, pellets 53 which are to be implanted in the animal. The pellets are retained in passageway 54 by covering the rear of the passageway with a removable tape and downwardly extending flexible finger 55 which is attached to barrel 52 and is pushed aside by the pressure of retraction. When the needle is loaded in the recess 16, the rod 28 abuts the next to last pellet 103 and when the needle is inserted, then withdrawn, the pellets are implanted under the animal's skin. Alternatively, a preloaded pellet-containing cylinder may be inserted into passageway 54. In such a case rods 28 must be of such a diameter to fit in the cylinder.

The dimensions of the needle 50 must be such that the needle can be readily subcutaneously inserted into the animal and the pellets 53 deposited. Since the pellets will generally be about 2.5-3.5 mm in diameter, preferably 3.0-3.2 mm, passageway 54 must be at least that diameter, preferably slightly more, (e.g. 1.08 times the pellet diameter) to accommodate the pellets. The overall length of the needle 50 is about 30 to 100 mm, preferably about 80-90 mm, while the diameter of tube 52 is about 2.7 to 4.0 mm. The enlarged part 60 of needle 50 will have a diameter of about 10 to 20 mm, and a length of about 5 to 30 mm, which will be sufficient to fit into recess 16 and be retained securely during the implanting procedure.

Turning now to FIG. 5, a cross-section of the apparatus depicted in FIG. 1 is seen. FIG. 5 depicts the apparatus in a cocked position ready to be utilized to implant the pellets subcutaneously in the animal. It can be seen that the carriage 10 is maintained in the forward part of track 4 by the tip 40 of trigger 32, thus maintaining spring 22 in a compressed condition. Needle 50 having enlarged portion 60 received and retained in recess 16 of carriage 10 is situate so that the passageway 54 which extends the length of needle 50 is aligned with passageway 18 and part way through passageway 54 to abut pellet 53 situate in passageway 54 of needle 50. Rod 28 is secured in a stationary position by rod retaining means 30 which is located in the back of track 4. As will be apparent from the Figures, rod 28 will have a diameter slightly smaller than that of passageways 18 and 54. The diameter of rod 28 may suitably be about 2 mm to about 8 mm, with passageways 18 and 54 being slightly larger to allow free movement of rod 28 therethrough.

A lip 17 extends longitudinally along the upper part of track 4 and fits into groove 15 extending longitudinally along carriage 10. This aids in supporting the carriage 10 and stabilizing in its rearward motion. The apparatus is utilized by inserting the sharp, beveled end of needle 50 subcutaneously into the animal, at least to the forward tip of rod 28, pulling trigger 32 which moves the tip 40 of trigger 32 downwardly thus releasing the carriage and allowing the spring 22 to expand and force the carriage rearwardly to the back 24 of track 4. The pellets 53 remain stationary while the needle 50 is witdrawn from around them and the pellets then remain under the skin of animal. Once the apparatus is cocked and ready to use, it can be prevented from going off by swinging safety catch 41 into groove 42 to thus prevent the movement of the trigger. Thus the apparatus can be readily located and unloaded without having the carriage move rearwardly by accidentally touching the trigger.

Preferably trigger 32 is equipped with a spring 45 to force the tip 40 of the trigger 32 upwardly when the carriage 10 is pushed forward sufficiently to allow the point 40 to snap up. The spring 45 is located in the back part of trigger 32 and is generally located within recess 43, located in trigger 32 and recess 44, located in handle 3.

The apparatus may be readily retained by the user by keeping it in a holster or by attaching a cable, rope, string, chain or the like to the handle 3 and placing the cable around the user's neck or wrist.

The apparatus of this invention is made of any suitable material such as metal or plastic, but is preferably prepared from a plastic material such as nylon, polycarbonate, high density polyethylene, high density polypropylene, ABS or other plastics which are capable of being injection molded. The apparatus can be injection molded by means well known in the art. Generally only five pieces of injection molded plastic will be needed. These consists of (1) a left half of the gun (having the handle 3 and track 4), (2) the right half of the gun (having the handle 3 and track 4), (3) a trigger mechanism 32, (4) a carriage 10, and (5) a front plate 24. In addition to the injection molded parts, the ejection rod 28 and guide rods 20 will be of metal for strength and durability. The springs 22 and 25 are also preferably metal. The rods are placed in the injection molded parts by having the properly placed groove in the injection molded parts in the back part 24 of track 2 and another groove in the front plate 24, which is then attached to the front part of the track with screws or glue. In assembling the apparatus, the trigger 32 and two halves are first connected with the trigger being mounted on the desired pivot point 33 and the spring 45 is placed within grooves 43 and 44 as desired. Once the two halves of the gun are together, rods 20 are placed in their respective grooves, springs 25 are slipped on, the carriage is inserted to allow the rods to extend through passageways 21 and to fit grooves 15 with lips 17, and springs 22 are placed on rods 20. Thereafter rods 20 are inserted as required in face plate 26 and the face plate is attached. Rod 28 and needle 50 are then inserted.

Alternatively, the gun can be prepared by using only four injection molded parts. These will include the two halves of the gun, the trigger means and the carriage. In this instance the face plate is an integral part of the half of the gun and is designed to have a groove running laterally so that rods 20 may slip into place by first placing the rods in an appropriate groove in the back plate and then sliding the front part of the rod into the lateral groove in the face plate after having placed the rod through the passageway 21 through extension 19 on carriage 10. After adjusting the carriage so that groove 15 corresponds to lip 17, the rods and springs are pushed into place, the halves are adjusted and attached. Rod 28 and needle 50 are thereafter inserted.

The needle is also manufactured by an injection molding technique using a five section mold as shown in the cross-section view in FIG. 6. If the needle is desired to have a tip which may be milled to a fine point, a plastic having a high percentage of filler is injected into the mold through injection port 109, for example, nylon with 5-25% by weight glass particles.

A five section mold as shown in the planar, vertical cross-section view of FIGS. 6 and 7, the sections being indicated as A, A′, B, C and D. In preparing the needle by injection molding, each of the parts or sections which comprise the mold must fit tightly together so that each of the fingers 101 are retained by each of the respective receiving holes 102 and that each face 100A, 100A′, 100B, 100C, 100D of each of the sections fits flush with the face of the adjoining section. Once the mold is assembled, the plastic is injected through injection port 109. The plastic fills void areas 105 and 104. Core 107 extends the entire length of the needle so that a hollow portion, which corresponds to 54 in FIGS. 4a-4e, is formed in the needle.

Referring more specifically to section A, the section employed for forming the tip of the needle, it can be seen that the metal tip can be placed on the needle either (a) after the needle has been injection molded and removed from the mold or (b) during the injection molding process.

(a) In the process wherein the metal tip is joined to the needle after the needle is formed and removed from the mold, the mode employed is shown in FIG. 7 as sections A and A′. Here, a curved projection 111 which is part of section A of the mold extends into free space 104 so that a void area around the outer tip of the needle is formed as shown in FIG. 9a as an end view along line 9a of FIG. 7. In FIG. 9a, 107 corresponds to the core and 111 corresponds to the projection in FIG. 7. Once the step of injecting the plastic into the form is completed and the plastic has hardened, the mold parts are separated and the plastic piece is ejected. In the mold shown in FIG. 7 the needle will have a recession in the tip into which a corresponding piece of metal will fit. The piece of metal corresponds to the shape indicated in FIG. 9a and is pointed so that a needle is obtained by placing the metal tip into recession formed by extension 111 and causing the metal to adhere. This can be done by placing a sufficient amount of glue in the recession so that the metal will be retained therein, or preferably, the metal is sonically welded to embed the metal in the plastic.

(b) Alternatively, the metal point may be placed in part A of the mold form prior to injection molding as shown in FIG. 8. Here the metal tip 103 is placed flush against the edge 112 of section A, and the plastic is injected. In order to get the metal to properly adhere to the plastic, small holes 114 through the metal in various places so that the plastic can flow through the holes and aid in retaining the metal to the tip of the needle. This is shown in FIG. 9b. Instead of holes passing through the metal tip as shown in FIG. 4c the metal tip can be designed so that there are inwardly extending extensions 116 as shown in FIG. 9c around which the plastic can flow and which retains the metal tip on the plastic needle.

The above explanation of the invention, along with the attached drawings, is given to explain how to make and use certain representative aspects of this invention, but is given as exemplary only and is not to be interpreted as limiting the scope of the appendant claims. Other equivalent means for performing the functions indicated may be apparent to one of skill in the art.

I claim as my invention:

1. An apparatus suitable for subcutaneously implanting at least one pharmaceutically acceptable pellet in an animal, which apparatus comprises handle means for grasping said apparatus with one hand;

a track attached to said handle means and having front and rear portions, said track being suitable for a carriage to move therealong;

a carriage placed within said track and movable therealong with front and rear portions corresponding to the front and rear portions of said track, said carriage having (i) a means in the front part of said carriage which is adapted to receive and retain a detachable needle having a passageway extending longitudinally through said needle, (ii) a passageway extending the length of said carriage parallel to the length of said track and corresponding to said needle passageway when said needle is received and retained by said carriage, and (iii) means to guide and stabilize said carriage along said track;

propelling means to propel said carriage along said track from the front part to the rear part of said track;

means attached to the rear part of said track to stop said carriage when propelled rearwardly;

means attached to the front part of said track to retain said carriage;

a straight, retractable rod attached to said stopping means so that the rod extends straight through said carriage passageway;

means to retain said rod stationary or allow said rod to be retracted;

a finger actuatable trigger attached to said handle which is designed to retain said carriage in a cocked position at the front part of said track and when actuated allows said carriage to be propelled rearwardly along said track and rod by force of said propelling means while said handle is held stationary with one hand.

2. The apparatus of claim 1 wherein said carriage exhibits a recess in its front part, which recess is adapted to receive and retain a flanged, detachable needle having a passageway extending the length of said needle.

3. The apparatus of claim 2 wherein received and retained in said carriage recess is a flanged needle having a barrel with a beveled, sharp end and an enlarged, flanged end; a passageway extending the length of said needle; and at least one pharmaceutically acceptable, implantable pellet in said needle passageway so that when said carriage is propelled rearwardly said rod extends beyond said sharp end of said needle.

4. The apparatus of claim 3 wherein a plurality of spherical, implantable pellets are in said needle passageway.

5. The apparatus of claim 3 wherein a flexible finger extends across the front part of said needle passageway to retain said pellet in said passageway.

6. The apparatus of claim 3 wherein the composition of said needle is nylon and glass particles.

7. The apparatus of claim 3 wherein said needle is plastic but has a metal tip to aid in penetrating said animal's skin.

8. The apparatus of claim 1 wherein said propelling means is a helical spring coil which is compressed when said carriage is in the cocked position and which expands when said trigger is actuated to propel said carriage rearwardly.

9. The apparatus of claim 1 wherein a portion of a metal rod is attached to the front end of said track, the unattached end of said metal rod being sufficiently sharp to penetrate said animal's skin.

10. The apparatus of claim 3 wherein a portion of a metal rod is attached to the front end of said track, the unattached end of said metal rod being sufficiently sharp to penetrate said animals skin, said metal rod being of substantially the same outside diameter as said needle and being at least as long as the portion of said needle extending beyond the front part of said track.

11. A process for subcutaneously implanting at least one biologically acceptable pellet in an animal using an apparatus including handle means for grasping said apparatus with one hand;

a track attached to said handle means and having front and rear portions, said track being suitable for a carriage to move therealong;

a carriage placed within said track and movable therealong with front and rear portions corresponding to the front and rear portions of said track, said carriage having (i) a recess in the front part of said carriage which is adapted to receive and retain a detachable needle having a passageway extending longitudinally through said needle, (ii) a flanged needle received and retained in said carriage recess, said needle having a barrel with a beveled, sharp end and an enlarged, flanged end, a passageway extending the length of said needle, and at least one pharmaceutically acceptable, implantable pellet in said needle passageway, (iii) passageway extending the length of said carriage parallel to the length of said track and corresponding to said needle passageway, and (iv) means to guide and stabilize said carriage along said track;

propelling means to propel said carriage along said track from the front part to the rear part of said track;

means attached to the rear part of said track to stop said carriage when propelled rearwardly;

means attached to the front part of said track to retain said carriage;

a straight, retractable rod attached to said stopping means so that the rod extends straight through said carriage passageway;

means to retain said rod stationary or allow said rod to be retracted;

a finger actuatable trigger attached to said handle which is designed to retain said carriage in a cocked position at the front part of said track and when actuated allows said carriage to be propelled rearwardly along said track and rod by force of said propelling means, which process comprises subcutaneously inserting said beveled, sharp end of said needle in said animal while said carriage is in the cocked position, forcing said needle subcutaneously to a depth corresponding to the tip of said rod, pulling said trigger while holding said handle stationary with one hand to allow said propelling means to move said carriage rearwardly and retract said needle from around said pellet so that said pellet(s) remain(s) subcutaneously implanted in said animal.

12. The process of claim 11 wherein a plurality of pellets are in said needle and are implanted in said animal simultaneously.

* * * * *